(12) United States Patent
Goetzl (10) Patent No.: US 9,933,440 B2
(45) Date of Patent: Apr. 3, 2018

(54) DRUG EFFICACY TEST METHOD FOR DEMENTIAS UTILIZING ASTROCYTE-DERIVED EXOSOMES

(71) Applicant: Edward J. Goetzl, San Francisco, CA (US)

(72) Inventor: Edward J. Goetzl, San Francisco, CA (US)

( * ) Notice: Subject to any disclaimer, the term of this patent is extended or adjusted under 35 U.S.C. 154(b) by 0 days.

(21) Appl. No.: 15/600,959

(22) Filed: May 22, 2017

(65) Prior Publication Data

US 2017/0343563 A1    Nov. 30, 2017

Related U.S. Application Data

(60) Provisional application No. 62/343,232, filed on May 31, 2016.

(51) Int. Cl.
*G01N 33/50* (2006.01)
*G01N 33/68* (2006.01)
*C12Q 1/68* (2018.01)

(52) U.S. Cl.
CPC ..... *G01N 33/6896* (2013.01); *G01N 33/5058* (2013.01); *C12Q 1/68* (2013.01); *C12Q 2600/136* (2013.01); *C12Q 2600/158* (2013.01); *G01N 33/50* (2013.01); *G01N 33/68* (2013.01); *G01N 2800/2814* (2013.01)

(58) Field of Classification Search
None
See application file for complete search history.

(56) References Cited

U.S. PATENT DOCUMENTS

| | | |
|---|---|---|
| 2012/0178177 A1 | 7/2012 | Delerive et al. |
| 2013/0005599 A1 | 1/2013 | Klass et al. |
| 2016/0041153 A1 | 2/2016 | Brown et al. |

FOREIGN PATENT DOCUMENTS

WO    2015075288 A1    5/2015

OTHER PUBLICATIONS

Winston et al., Alzheimer's & Dementia: Diagnosis, Assessment & Disease Monitoring 3 (2016) 63-72, published online May 7, 2016.*
Fiandaca, Massimo S. et al: Article—"Identification of Preclinical Alzheimer's Disease by a Profile of Pathogenic Proteins in Neurally Derived Blood Exosomes: A Case-Control Study", Elsevier, Alzheimer's & Dementia, 2014, 1-8.
Goetzl, Edward J. et al: Article—"Altered Lysosomal Proteins in Neural-Derived Plasma Exosomes in Preclinical Alzheimer Disease", Neurology, Jul. 7, 2015, 85(1): 40-47.
Kapogiannis, Dimitrios et al: Article—"Dysfunctionally Phosphorylated Type 1 Insulin Receptor Substrate in Neural-Derived Blood Exosomes of Preclinical Alzheimer's Disease", The FASEB Journal, Published Online Oct. 23, 2014; article fj. 14-262048.
Goetzl, Edward J. et al: Article—"Low Neural Exosomal Levels of Cellular Survival Factors in Alzheimer's Disease", Annals of Clinical and Translational Neurology, Jul. 2015, 2(7): 769-773. Published Online May 13, 2015.
Goetzl, Edward J. et al: Article "Human Plasma Platelet-Derived Exosomes: Effects of Aspirin", The FASEB Journal, vol. 30, No. 5, pp. 2058-2063, Published Online Feb. 12, 2016.
Abner, Erin L. et al: Article—"Plasma Neuronal Exosomal Levels of Alzheimer's Disease Biomarkers in Normal Aging", Annals of Clinical and Translational Neurology, May 2016, 3(5): 399-403. Published Online Apr. 13, 2016.
Winston, Charisse N. et al: Article—"Prediction of Conversion From Mild Cognitive Impairment to Dementia With Neuronally Derived Blood Exosome Protein Profile", Elsevier, Alzheimer's & Dementia: Diagnosis, Assessment & Disease Monitoring, 3 (2016) pp. 63-72.
Katja M. Kanninen et al.: Article—"Exosomes As New Diagnostic Tools in CNS Diseases", Elsevier, Biochimica at Biophysica Acta 1862 (2016) 403-410.

* cited by examiner

*Primary Examiner* — Kimberly Ballard
*Assistant Examiner* — Stacey N MacFarlane
(74) *Attorney, Agent, or Firm* — Breiner & Breiner, L.L.C.

(57) ABSTRACT

Non-invasive method for diagnosing or prognosing Alzheimer's disease, frontotemporal dementia, or other dementia involving isolating astrocyte-derived exosomes (ADEs) and neuron-derived exosomes (NDEs) from a human biological sample (i.e., plasma, serum, urine or cerebrospinal fluid), analyzing cargo extracts of the ADEs and NDEs to detect at least one specified protein or microRNA biomarker, comparing the levels and activities of detected biomarker(s) to those in control samples to identify a statistically significant difference between the detected biomarker(s) and corresponding biomarker(s) in the control sample to determine presence of Alzheimer's disease, frontotemporal dementia, or other dementia; and testing effects of drugs on levels and activities of each biomarker, as well as effects of drugs administered to test subjects on levels and activities of each biomarker in ADEs and NDEs from subsequently obtained biological samples.

5 Claims, 6 Drawing Sheets

DRUG EFFICACY TEST METHOD FOR DEMENTIAS UTILIZING ASTROCYTE-DERIVED EXOSOMES

RELATED APPLICATION

The present application claims benefit of U.S. Provisional Patent Application Ser. No. 62/343,232 filed May 31, 2016, which is incorporated herein by reference.

FIELD OF INVENTION

Method for non-invasive isolation of astrocyte-derived exosomes; method involving central nervous system astrocyte-derived exosomes to diagnose or predict Alzheimer's disease or other dementia in a test subject; and method involving pathogenic proteins from astrocyte-derived exosomes as indicator of efficacy of drug in treatment of Alzheimer's disease or other dementia.

BACKGROUND OF THE INVENTION

Millions of people today have Alzheimer's disease or some other form of dementia, such as frontotemporal dementia. Generally, definitive diagnostic testing is not possible since such involves testing of brain tissue. Other testing, which is also both costly and not practical, is not accurate and is done after symptoms of dementia have occurred and, thus the disease generally has already progressed significantly. This decreases the chance of effectively treating the disease since, at this time, no cure exists for dementia and treatments available are to slow the progression of the disease. Therefore, a need exists for a non-invasive method to predict or diagnose Alzheimer's disease and other dementias in a person prior to onset of the dementia so as to allow for earlier treatment to slow the onset or to lessen the effects of the disease. Additionally, a need exists for drug indicator tests that confirm mechanism of action of a drug and measure the extent of the effect of a given drug in treating Alzheimer's disease or other dementia with recipient patient specific efficacy.

Astrocytes or astroglial cells in the brain and spinal cord are distinguished by their star shape and prominent network of intermediate filaments, consist of numerous subsets, and are rich in glial fibrillary acidic protein (GFAP), glutamine synthetase (GluSyn) and vimentin. They are the most abundant central nervous system (CNS) glial cells with a frequency approximately five-times that of neurons and are functionally associated with neuronal synapses. Signals from several neural proteins, such as sonic hedgehog (SHH), may contribute to the diversity of astrocyte phenotypes. In addition, astrocytes may be activated to different functional states by various mediators, such as interferon-$\gamma$ and cyclic guanosine-adenosine monophosphate (cGAMP). Astrocytes have many supportive neuronal functions including supplying nutrients, regulating extracellular ion concentrations, releasing neurotransmitters such as glutamate and adenosine triphosphate (ATP), inhibiting synaptic transmission by adenosine derived from ATP, and promoting the myelinating activity of oligodendrocytes through leukemia inhibitory factor released in response to ATP. Astrocytes also may facilitate repair of injuries to the CNS, in part by transformation into neurons, and appear to maintain some brain neural stem cells in a dormant state by secretion of several specific mediators.

Astrocytes accumulate at sites of deposition of A$\beta$ peptides in the brain, where they internalize and degrade these peptides in an apparently protective process requiring expression of apolipoprotein E. At high intra-cellular and intra-nuclear levels, A$\beta$ peptides modify many astrocyte activities ranging from mitochondrial functions to protein transcription. However, it has only recently been appreciated that some subsets of astrocytes also contain the amyloid precursor protein (APP), $\beta$-secretase, termed $\beta$-site APP cleaving enzyme 1 (BACE-1), and $\gamma$-secretase required for generation of A$\beta$ peptides from APP, and that levels of these components in astrocytes are increased by fibrillary A$\beta$42 and several inflammatory cytokines. In the same studies, microglia contained none of these proteins of the A$\beta$ peptide-generating pathway. Mechanisms of regulation of expression of BACE-1 involve several transcriptional elements, such as Sp1 and NFAT3, as well as post-transcriptional events. BACE-1 stability and function also are influenced by other neural proteins, including ubiquilin-1 and septin-8. A greater understanding of the relative role of these astrocyte pathways in generation of A$\beta$ peptides in the brain has come from recent analyses of human induced pluripotent stem cell-derived neural cells. With these methods, astrocytes were shown to secrete high levels of A$\beta$ peptides and astrocyte-like cells were prominently represented among the highest producers of A$\beta$ peptides.

SUMMARY OF THE INVENTION

The invention involves diagnostic or predictive methods and drug efficacy testing methods including low risk simple analyses of non-invasively obtained biological samples of human plasma, serum, urine or cerebrospinal fluid (CSF). The non-invasive human plasma and other fluid processing methods of the invention include total exosome physicochemical precipitation and immunochemical isolation of CNS astrocyte-derived exosomes (ADEs) from a total population of exosomes in the biological sample.

Further, the invention includes a method involving measuring certain biomarkers in extracts of ADEs to confirm the identity of the ADEs, and to provide indication or lack of indication of Alzheimer's disease (AD), frontotemporal dementia (FTD), or other dementia in a test subject and to distinguish one type of dementia from another type of dementia.

Further the invention includes a method involving extracts from ADE wherein the extracts contain certain pathogenic proteins and microRNAs (miRNAs) as drug targets under simple analytical testing conditions (e.g., laboratory testing) to determine the degree to which a given drug is beneficially effective in treating AD, FTD or other dementia by inhibiting generation and/or actions of these pathogenic proteins. Such testing methods can be arranged to provide for serial testing of samples of pathogenic proteins or miRNAs in exosomes of fluids taken sequentially over time from a human test subject to assess effectiveness of different drugs as therapeutic agents for treating AD, FTD or other dementia.

The methods of the invention include providing a plasma or other fluid sample from a human test subject. Thereafter, isolating specific subsets of exosomes from the total population of exosomes in the plasma sample, namely, isolating astrocyte-derived exosomes (ADEs) and neuron-derived exosomes (NDEs). Analyzing by assay the exosomes to detect at least one protein biomarker or miRNA biomarker, i.e., pathogenic protein or miRNA, of AD or FTD or other dementia being targeted. The level(s) present of the detected biomarker(s) is(are) then compared as between the ADE and NDE of the test sample, and a control sample to determine whether AD or FTD or other dementia targeted are indicated to be present in the human test subject from which the biological fluid sample was obtained. The levels to be indicative of the presence of AD, FTD, or other dementia need have a statistically significant difference between the level(s) of the detected protein or miRNA biomarker(s) and the level(s) of the same biomarker(s) in the control sample. A level is considered herein to have a "statistically significant difference" if the level of the biomarker in a sample from the test subject differs from the level of the control by an amount greater than the standard error of the assay used to assess the biomarker and the control, and preferably is at least 10%, and more preferably at least 25%, or 50%, or 75%, or 100%. The "control" or "control sample" is a material comprising none or a normal level of one or more of the protein or miRNA biomarker of the invention so that the control can serve as a comparator against which a corresponding biomarker from the test subject can be compared.

The protein biomarkers determined to be indicative in the methods of the invention are CD81 (a tetraspanning human exosome marker), GFAP (glial fibrillatory acidic protein), glutamine synthetase (GluSyn), NF-Lch (neuro-filament light chain), NS-E or NS-enolase (neuron-specific enolase), BACE-1 (β-site amyloid protein cleaving enzyme 1), γ-secretase, sAPPβ, sAPPα, Aβ42, P-T181-tau, P-S396-tau, ubiquilin-1, and septin-8. A miRNA, which is a valuable biomarker for CNS damage in dementias, present in ADEs and NDEs is miRNA9.

Assays suitable for use in analyzing the ADE and NDE cargo proteins and cargo miRNAs include ELISAs (enzyme-linked immunosorbent assays), Western blots, mass spectrometry, and other assays known to one skilled in the art.

The invention also includes a kit for diagnosing AD, FTD, or other dementia comprising a reagent for measuring the level of the biomarker(s) (e.g., protein and miRNA biomarkers) in the exosomes isolated from a biological sample (e.g., plasma, serum, urine or CSF) of the test subject. The kit includes a polymer for precipitation of a total set of plasma/serum/etc. exosomes; an antibody (biotin-conjugated) for absorption with biotin-binding resin beads that pellet antibody-bound exosomes; an acidic solution to release exosomes from the antibody-resin complex; and a solution to extract protein cargoes or miRNA cargoes. A detergent solution is suitable for extracting protein cargoes.

DESCRIPTION OF THE DRAWINGS

FIGS. 1A-1E relate to the experimental examples described below and show components of the Aβ42 peptide-generating system in ADEs and NDEs. Each point depicts the value for one test subject or control subject and the mean for each group of points is shown by a solid horizontal line. The mean±S.E.M. levels in picograms/milliliter (pg/ml) are, (where "AC"=Alzheimer's disease control and "FTC"=frontotemporal dementia control): BACE-1 ADEs—AC, 209±16.4; AD, 398±81.6; FTC, 211±18.0; FTD, 233±27.5; NDEs—AC, 26.9±0.74; AD, 23.3±1.70. γ-secretase ADEs—AC, 1406±154; AD, 1329±131; FTC, 1317±109; FTD, 1357±140; NDEs—AC, 82.1±14.1; AD, 83.4±15.0. sAPPα ADEs—AC, 187±27.4; AD, 191±30.5; FTC, 284±22.2; FTD, 150±18.4; NDEs—AC, 18.1±1.10; AD, 23.3±0.76. sAPPβ ADEs—AC, 6048±483; AD, 11243±1747; FTC, 4684±605; FTD, 5127±547; NDEs—AC, 2266±112; AD, 2992±184. Septin-8 ADEs—AC, 1843±269; AD, 497±86.6; FTC, 1183±109; FTD, 1152±144; NDEs—AC, 308±36.7; AD, 350±26.3. Statistical significance of differences between disease and control groups for ADEs are shown above the disease group clusters of ADE data and those between values in NDEs and corresponding values in ADEs are shown above the clusters of NDE data; where +, $p<0.05$, *, $p<0.01$, and **, $p<0.001$.

FIGS. 2A-2C show primary pathogenic proteins of AD in ADEs and NDEs. Each point depicts the value for one test subject or control subject and the mean for each group of points is shown by a solid horizontal line. The mean±S.E.M. levels in pg/ml are: P-T181-tau ADEs—AC, 496±76.0; AD, 355±60.4; NDEs—AC, 6.55±0.94; AD, 66.0±7.47; P-S396-tau ADEs—AC, 116±20.2; AD, 111±32.1; NDEs—AC, 9.76±0.75; AD, 24.1±2.63; Aβ42 ADEs—AC, 56.6±9.25; AD, 30.9±4.38; NDEs—AC, 4.43±0.25; AD, 7.58±0.25. Statistical significance of differences between disease and control groups for ADEs are shown above the disease group clusters of ADE data and those between values in NDEs and corresponding values in ADEs are shown above the NDE clusters of data; where +, $p<0.05$, *, $p<0.01$, and **, $p<0.001$.

DETAILED DESCRIPTION OF THE INVENTION

Methods for non-invasive diagnosis and prognosis of Alzheimer's disease (AD) frontotemporal dementia (FTD), and other dementias are desired and needed, in particular for diagnosis and prognosis prior to onset of symptoms. No cure currently exists for AD, FTD, and other dementias and treatments of such disease therefore are directed to delaying or lessening of the effects of the dementia. Accordingly, the ability to commence early with treatment is beneficial since once the physical manifestations occur in a person, such are not reversible. The methods of the invention are particularly desirable as providing diagnostics and drug efficacy testing by low risk simple analyses of small blood samples allowing both access to anatomical areas not susceptible to biopsies and obtaining an integrated sample that reflects all areas of the brain in conditions, such as AD, where abnormalities are unpredictably focal and can be missed by a biopsy.

The methods of the invention are directed to diagnosis or prognosis in a human test subject of AD, FTD, or other dementia based on obtaining a non-invasive plasma or other biological fluid sample from a person and subjecting this sample to low risk simple analysis in a laboratory setting. If a diagnosis is made or prognosis projected for AD, FTD, or other dementia, the pathogenic material detected can be used to determine the efficacy of one or more drugs targeted to eradicate the pathogenic material.

The biological fluid sample (e.g., plasma, serum, urine or CSF) is treated to isolate select exosomes from a total population of exosomes precipitated from the biological fluid sample, namely selective immunochemical isolation of central nervous system (CNS) astrocyte-derived exosomes (ADEs) and CNS neuron-derived exosomes (NDEs). The ADEs and NDEs are separately isolated using different antibodies specific for exosome-surface proteins that came from their respective CNS cells of origin to absorb/pellet these distinct subsets. The preferred immunoisolation of ADEs is by using the anti-GLAST antibody, and of NDEs is by using the L1CAM antibody. The anti-GLAST antibody serves to detect astrocytes based on the expression of GLAST. The L1CAM antibody serves to recognize certain polypeptides of L1CAM corresponding to the full length protein.

The exosomal cargo proteins or miRNAs are then analyzed by multiple assays, preferably ELISAs, to detect at least one, but preferably multiple, protein biomarkers or miRNA biomarkers in the ADEs and NDEs. The one or more protein biomarkers sought to be detected are CD81, GFAP, GluSyn, NF-Lch, NS-enolase, BACE-1, γ-secretase, sAPPβ, sAPPα, Aβ42, P-T181-tau, P-S396-tau, ubiquilin-1, and septin-8. A miRNA found to be a valuable biomarker for dementias in ADEs and NDEs is miRNA9.

The detected protein or miRNA biomarker(s) and corresponding marker(s) in a control sample are then compared to locate a statistically significant difference between the detected selected biomarker(s) and the control marker(s) to determine a diagnosis of AD, FTD, or other dementia. The levels are considered as having a "statistically significant difference" if the level of the marker in a sample from the test subject differs from the level of the control by an amount greater than the standard error associated with the assay used to assess the marker, preferably at least a 10% difference and more preferably at least 25%, 50%, 75% or 100% difference in levels.

The "control" or "control sample" is a material comprising none or a normal (i.e., in an acceptable range) level for a cognitively healthy human subject of one or more of the protein or miRNA biomarkers of the invention so that the control sample can serve as a comparator against which level(s) in the biological sample can be compared.

The comparison of quantities of the detected protein or miRNA biomarker(s) in the test subject exosomes and the control subject exosomes sample (as obtained from sources known in the art) is to locate a statistically significant difference between the detected biomarker and control biomarker to determine the presence of AD, FTD, or other dementia in the test subject. The statistically significant difference can be an increased or decreased amount as between levels.

If a diagnosis or prognosis of AD, FTD, or other dementia is made, this allows for the provision of a treatment regimen for the test subject. This can include further testing of the biological fluid sample from the test subject to determine the efficacy of a given drug against levels and activities of selected biomarkers of the sample. While both ADEs and NDEs are useful in drug efficacy testing, the best drug candidates to date affect biomarkers in ADEs most. For drug testing of exosome samples, preferably included are protein amounts/levels and protein activities (e.g., BACE-1 protein amount/level and its protease/enzymatic activity). ADEs and NDEs are isolated from a pre-drug biological (e.g., plasma/serum) sample and tested with the drug to see if the drug has a beneficial effect. If the drug has a beneficial effect, then sequential biological fluid samples are obtained at intervals during drug treatment for isolation of ADEs and NDEs and assessment made of their biomarkers to see if the drug is having its desired effect(s) in vivo in the recipient.

EXPERIMENTAL EXAMPLES

I. ADE and NDE in Treatment of AD

To exemplify the invention, the amyloidogenic potential of distinct sets of human neural cells was examined by quantifying proteins and products of the Aβ peptide-generating system in neuron-derived exosomes (NDEs) and astrocyte-derived exosomes (ADEs) precipitated and separately immunochemically enriched from plasmas of test subjects with AD or FTD and their matched cognitively normal controls. ADE levels of BACE-1, γ-secretase, sAPPβ, sAPPα, Aβ42, P-T181-tau and P-S396-tau were all significantly three- to 17-fold higher in ADEs than NDEs of test subjects and controls. Levels of only BACE-1 and sAPPβ were significantly higher in ADEs of AD test subjects than control subjects, but not of FTD test subjects than controls. Levels of sAPPβ, sAPPα, Aβ42, P-T181-tau and P-S396-tau were significantly higher in NDEs of AD test subjects than control subjects. The precise profile of ADE cargo proteins is useful in indicating drugs which will be effective in treatments of AD.

Test Subject and Control Subject Selection and Evaluation.

Twelve (12) test subjects were identified with amnestic mild cognitive impairment (aMCI) or early dementia from AD, 16 patients with behavioral variant FTD (bFTD) and 28 age- and gender-matched cognitively-normal controls, who had donated blood in the Clinical Research Unit of the National Institute on Aging (NIA), Baltimore, Md., the Jewish Home of San Francisco (JHSF), San Francisco, Calif. or the Memory and Aging Center of the University of California, San Francisco (UCSF), San Francisco, Calif. This information is show in Table 1 below.

TABLE 1

Characteristics of Test Subjects and Control Subjects
Distinctive protein markers of plasma astrocyte-derived exosomes
(ADEs) as contrasted with plasma neuronal-derived exosomes (NDEs)

| Diagnosis[1] | Total Number | Male/Female | Ages Mean ± S.E.M. | Cognitive State MMSE[2] Scores Means ± S.E.M. |
|---|---|---|---|---|
| AD | 12 | 6/6 | 74.4 ± 1.98 (S.D. = 6.84) | 26.3 ± 0.99* (S.D. = 3.45) |
| AC | 12 | 6/6 | 74.4 ± 1.98 (S.D. = 6. 84) | 29.8 ± 0.11 (S.D. = 0.39) |
| FTD | 16 | 12/4 | 63.6 ± 1.82 (S.D. = 7.27) | 19.7 ± 2.57** (S.D. = 10.3) |
| FTC | 16 | 12/4 | 63.6 ± 1.82 (S.D. = 7.27) | 29.9 ± 0.09 (S.D. = 0.34) |

[1]AD, AC, FTD and FTC are the test subjects and corresponding controls with Alzheimer's disease and Frontotemporal dementia respectively.
[2]MMSE = Mini-Mental State Examination.
The significance of differences between cognitive state (MMSE) values of the test subjects and control subjects with each type of dementia was calculated by an unpaired t test for AD vs. AC and FTD vs. FTC;
*= $p < 0.01$ and
**= $p < 0.001$.

Test subjects and normal control subjects had mental status testing before blood sampling, and most test subjects had measurements of CSF Aβ1-42, total tau and P-T181-tau when first diagnosed with dementia.

Test subjects were classified as having aMCI from AD according to the Petersen criteria and had a Clinical Dementia Rating (CDR) global score of 0.5 ("Mild Cognitive Impairment as a Diagnostic Entity", *J. Intern. Med.*, R. C. Petersen, (256) pages 183-194 (2004), and "Toward Defining the Preclinical Stages of Alzheimer's Disease: Recommendations from the National Institute on Aging-Alzheimer's Association Workgroups or Diagnostic Guidelines for Alzheimer's Disease", *Alzheimer's Dement.*, R. A. Sperling et al., (7) pages 280-292 (2011) [each of these articles being incorporated herein by reference]). Those with mild dementia and probable AD were diagnosed by the Dubois criteria and had a CDR global score of 1.0 ("Research Criteria for the Diagnosis of Alzheimer's Disease: Revising the NINCDS-ADRDA Criteria", *Lancet Neurol.*, B. Dubois et al., (6) pages 734-746 (2007), and "Clinical Diagnosis of Alzheimer's Disease: Report of the NINCDS-ADRDA Work Group Under the Auspices of Department of Health and Human Services Task Force on Alzheimer's Disease", *Neurology*, G. McKhann et al., (34) pages 939-944 (1984), [each of these articles being incorporated herein by reference]). A CSF level of Aβ1-42<192 pg/ml supported a diagnosis of AD ("Cerebrospinal Biomarker Signature in Alzheimer's Disease Neuroimaging Initiative Subjects", *Ann. Neurol.*, L. M. Shaw et al., (65) pages 403-413 (2009), [this article being incorporated herein by reference]). Mini-mental state examination (MMSE) and the Alzheimer's disease assessment scale-cognitive subscale (ADAS-cog) were conducted as described in "Predictors of Placebo Group Decline in the Alzheimer's Disease Assessment Scale-Cognitive Subscale (ADAS-Cog) in 24 Week Clinical Trials of Alzheimer's Disease", *J. Alzheimer's Dis.*, M. C. Irizarry et al., (14) pages 301-311 (2008), and "The ADAS-Cog in Alzheimer's Disease Clinical Trials: Psychometric Evaluation of the Sum and Its Parts", *J. Neurol. Neurosurg. Psychiatry*, S. J. Cano et al., (81) pages 1363-1368 (2010) [each of these articles being incorporated herein by reference]. Test subjects with bFTD had been evaluated at the Memory and Aging Center of UCSF. Their diagnosis and assessment (Table 1) were based on standard clinical and mental status criteria, including discriminant analyses of neuropsychiatric and other elements that distinguish bFTD from AD ("Sensitivity of Revised Diagnostic Criteria for the Behavioral Variant of Frontotemporal Dementia", *Brain*, K. Rascovsky et al., (134) pages 2456-2477 (2011), and "Classification of Primary Progressive Aphasia and Its Variants", *Neurology*, M. L. Gorno-Tempini et al., (76) pages 1006-1014 (2011) [each of these articles being incorporated herein by reference]).

Ten ml of venous blood were drawn into 0.5 ml of saline with EDTA or 100 U/ml of heparin, incubated for 10 min at room temperature and centrifuged for 15 min at 2500×g. Plasmas were stored in 0.5 ml aliquots at −80° C. Laboratory studies were performed without knowledge of donor identity.

Exosome Isolation from Plasma for Extraction and ELISA Quantification of Cargo Proteins.

One-fourth ml aliquots of plasma from frozen stocks each was defrosted, received 0.1 ml of thromboplastin, and was incubated for 60 min at room temperature with mixing before addition of 0.15 ml of Dulbecco's calcium- and magnesium-free salt solution containing the suggested final concentrations of protease inhibitor cocktail (Roche Applied Sciences, Inc., Indianapolis, Ind.) and phosphatase inhibitor cocktail (Pierce Halt, Thermo-Fisher Scientific, Inc., Rockford, Ill.) ("Identification of Preclinical Alzheimer's Disease By a Profile of Pathogenic Proteins in Neurally Derived Blood Exosomes: A Case-Control Study", *Alzheimers Dement.*, M. S. Fiandaca et al., (11) pages 600-607, e601 (2015), and "Altered Lysosomal Proteins in Neural-Derived Plasma Exosomes in Preclinical Alzheimer Disease", *Neurology*, E. J. Goetzl et al., (85) pages 40-47 (2015) [each of these articles being incorporated herein by reference]). After mixing contents at room temperature for 10 min, all tubes were centrifuged at 3,000×g for 20 min at 4° C. ExoQuick exosome solution (EXOQ; System Biosciences, Inc., Mountain View, Calif.) was added at 126 µL per tube followed by incubation for 60 min at room temperature to precipitate total exosomes as described in *Neurology* (85) pages 40-47, supra. Each exosome pellet was re-suspended in 350 µl of distilled water with inhibitor cocktails before immunochemical enrichment of exosomes from neural sources.

Exosome suspensions were incubated for 1 hr. at 4° C. with 1.5 µg of mouse anti-human GLAST (ACSA-1) biotinylated antibody (Miltenyi Biotec, Inc., Auburn, Calif.) in 50 µL of 3% BSA (1:3.33 dilution of Blocker BSA 10° solution in $DBS^{-2}$ [Thermo Scientific, Inc.]) per tube with mixing, followed by addition of 10 µl of streptavidin-agarose ultralink resin (Thermo Scientific, Inc.) in 40 µL of 3% BSA and incubation for 30 min at 4° C. After centrifugation at 400×g for 10 min at 4° C. and removal of the supernate, each pellet was suspended in 100 µL of 0.05 M glycine-HCl (pH 3.0) by gentle mixing for 10 sec and centrifuged at 4,000×g for 10 min at 4° C. Supernatants then were transferred to clean tubes containing 50 µL of 10% BSA and 10 µL of 1 M Tris-HCl (pH=8.0) and mixed. Then, each tube received 0.59 ml of M-PER mammalian protein extraction reagent (Thermo Scientific, Inc.), that had the cocktails of protease and phosphatase inhibitors at recommended concentrations. These suspensions were incubated at room temperature for 10 min before storage at −80° C. until use in ELISAs (enzyme-linked immunosorbent assays).

Exosome proteins were quantified by human ELISA kits for NF-Lch, Aβ42, γ-secretase and the tetraspanning exosome marker CD81 (American Research Products-Cusabio, Waltham, Mass.) with verification of the CD81 antigen standard curve using human purified recombinant CD81 antigen (Origene Technologies, Inc., Rockville, Md.), GluSyn (American Research Products-Cloud Clone, Ltd., Waltham, Mass.), type 1 neural cell adhesion molecule (NCAM-1) (RayBiotech, Inc., Norcross, Ga.), neuron-specific enolase (NS-enolase) (R&D Corp., Minneapolis, Minn.), BACE-1 and total APP (Fivephoton Biochemicals, San Diego, Calif.), glial fibrillary acidic protein (GFAP) (EMD-Millipore Corp., Billerica, Mass.) P-T181-tau and P-S396-tau (Life Technologies-Thermo-Fisher, Inc., Carlsbad, Calif.) according to suppliers' directions. The mean value for all determinations of CD81 in each assay group was set at 1.00 and the relative values for individual samples used to normalize their recovery.

Exosome Counts.

Each suspension of extracellular vesicles was diluted 1:200 in PBS. The mean diameter (nm) and concentration (particles/ml) of extracellular vesicles in each suspension were determined using the Nanosight NS500 system with a G532 nm laser module and NTA 3.1 nanoparticle tracking software (Malvern Instruments, Malvern, UK). Camera settings were: gain 366; shutter 31.48; frame rate 24.9825 fps/s; Brownian motion was captured by five repeated 20 sec video recordings.

Statistical Analyses.

The statistical significance of differences between means for cross-sectional test subject groups and between each test subject group and their respective control group was determined with an unpaired Student's t-test including a Bonferroni correction (GraphPad Prism 6, La Jolla, Calif.). The discriminatory ability of each exosomal protein is presented using Receiver Operating Characteristic (ROC) analyses with Confidence Intervals estimated based on the Binomial Exact distribution (STATA 13.1). Discriminant classifier analyses were performed to evaluate the conjoint ability of exosomal proteins to differentiate the diagnostic groups (STATA 13.1). For longitudinal analyses, the significance of differences between serial values for $AD_1$-$AD_2$ and $FTD_1$-

FTD$_2$ test subjects taken before and after onset of MCI or dementia was calculated with a paired t-test (GraphPad).

Results.

Plasma astrocyte-derived exosomes (ADEs) are significantly less numerous than plasma neuron-derived exosomes (NDEs) for AD test subjects and matched controls based on exosome counts and exosome extract levels of CD81 per ml of plasma as shown in Table 2.

section A). In NDEs, levels of CD81 are lower in AD test subjects than AC controls (p=0.022), whereas CD81-normalized levels of all other protein markers are higher for AD test subjects than AC controls (p<0.001 for all) (Table 2, section B).

Levels of components of the pathological Aβ42-generating system, including BACE-1 and γ-secretase, as well as the initial APP cleavage fragment of BACE-1 designated

TABLE 2

Distinctive Protein Markers of Plasma ADEs as Contrasted with Plasma NDEs

| | Exosome Counts | Analyte (pg/ml) | Analyte (pg/ml) | Analyte (pg/ml) Plasma Source | Analyte (pg/ml) | Analyte (pg/ml) |
|---|---|---|---|---|---|---|
| | (×10$^9$/ml) | CD81 | GFAP[1] | GluSyn[2] | NF-Lch[3] | NS-E[4] |
| A. ADEs | | | | | | |
| Alzheimer's Disease | 69.8 ± 14.9 | 1305 ± 100 | 33533 ± 1976 * | 672 ± 145 | 94.8 ± 7.89 | 295 ± 25.7 |
| Matched Controls | 88.5 ± 16.1 | 1074 ± 56.1 | 59708 ± 6869 | 660 ± 137 | 104 ± 4.21 | 291 ± 30.5 |
| B. NDEs | | | | | | |
| Alzheimer's Disease | 229 ± 49.2 ** | 4269 ± 234 ** | 8395 ± 817 ** | 42 ± 7.03 * | 1412 ± 56.9 ** | 6024 ± 139 ** |
| Matched Controls | 307 ± 53.4 ** | 5154 ± 257 ** | 2016 ± 267 ** | 53 ± 8.49 * | 1075 ± 37.6 ** | 3383 ± 131 ** |

[1]GFAP = Glial Fibrillary Acidic Protein.
[2]GluSyn = Glutamine synthetase.
[3]NF-Lch = Neurofilament light chain.
[4]NS-E = Neuron-specific enolase.

As to Table 2, each value is mean±S.E.M. of values for 12 test subjects per group, except for exosome counts that are for 8 test subjects per group. Levels of GluSyn, GFAP, NF-Lch and NS-E were normalized to the levels of CD81 in the same samples. Statistical significance was calculated with a two-sample t test where *=p<0.01 and **=p<0.001. The asterisks in B. indicate significantly higher or lower values than for the corresponding levels in A. and the asterisk in A. shows the level of significance of the difference between ADE GFAP levels in AD test subjects and matched controls. In NDEs, levels of CD81 (p=0.022) and GluSyn (not significant) are lower, whereas those of GFAP, NF-Lch and NS-E are higher (p<0.001) in AD test subjects than matched controls.

For FTD test subjects, mean (±SEM) counts of recovered ADEs were 86.0±12.9×10$^9$/ml of plasma, that were no different from those of FTC controls at 82.5±14.3×10$^9$/ml. CD81 levels for FTD test subjects and FTC controls were indistinguishable at 1145±75 and 1498±157 pg/ml, respectively. ADEs have the same size distribution as NDEs, with respective mean (±SEM) diameter values of 196±10.8 nm and 165±27.6 nm for AD test subjects and 189±21.0 nm and 173±15.4 nm for matched controls. For FTD test subjects and FTC controls, these values also were similar at 224±11.5 nm 171±14.8 nm, respectively.

CD81-normalized levels of the astrocyte marker GFAP are significantly higher in ADEs than NDEs. GFAP has been detected previously in neurons in relation to aging, hypoxia or neurodegeneration ("Neuronal Expression of GFAP Splice Forms", *Mol. Psychiatry*, E. M. Hol et al., (8) pages 786-796 (2003), and "Cortical Glial Fibrillary Acidic Protein-Positive Cells Generate Neurons After Perinatal Hypoxic Injury", *J. Neurosci.*, B. Bi et al., (31) pages 9205-9221 (2011) [each of these articles being incorporated herein by reference]). Levels of the neuronal markers NF-Lch and NS-enolase are significantly higher in NDEs than ADEs (Table 2). CD81-normalized levels of GFAP in ADEs are lower for AD test subjects than AC controls (Table 2, sAPPβ all were significantly higher in ADEs than NDEs of both AD patients and their matched AC controls (p<0.0001) (FIGS. 1A-1E). Further, levels of the initial APP cleavage fragment of α-secretase in the physiological pathway of APP proteolysis designated sAPPα also were significantly higher in ADEs than NDEs of both AD test subjects and their matched AC controls (p<0.0001). ADE levels of BACE-1, the initial protease constituent of the pathological system, were significantly higher in AD test subjects (398±81.6 pg/ml, mean±SEM) than matched AC controls (207±16.4 pg/ml), whereas no such difference was found for the lower BACE-1 levels in NDEs. BACE-1 levels in ADEs of AD test subjects were marginally higher than in ADEs of FTD test subjects (p=0.046), but those in ADEs of FTD test subjects were no different than in ADEs of their matched FTC controls (FIGS. 1A-1E). In contrast, neither ADE levels nor the much lower NDE levels of γ-secretase differed significantly between AD test subjects and matched AC controls, and γ-secretase levels in ADEs of FTD test subjects were indistinguishable from those of their matched FTC controls and from those of AD test subjects (FIGS. 1A-1E). The higher levels of BACE-1 in ADEs of AD test subjects than AC controls are reflected in the significantly higher ADE levels of the BACE-1 pathological cleavage product of APP, sAPPβ, for AD test subjects as compared with AC controls (p=0.0159). The much lower levels of sAPPβ in NDEs also are significantly higher for AD test subjects than AC controls (p=0.0028). In contrast, there is no difference between ADE levels of sAPPβ in FTD test subjects compared with FTC controls. ADE levels of the physiological cleavage product of APP, sAPPα, showed no difference between AD test subjects and AC controls, whereas the much lower NDE levels of sAPPα were significantly higher in AD test subjects than AC controls (p=0.0008) and ADE levels of sAPPα were higher in FTC controls than in FTD test subjects (p<0.0001). The neural protein septin-8 has been implicated in normal synaptic plasticity and in the regulation of amyloidogenic processing of APP through control of sorting and expression of BACE-1. ADE levels of septin-8 are significantly lower in AD test subjects than AC controls ($p<0.0001$) and in AD test subjects than in FTD test subjects ($p=0.0009$), but no different in ADEs of FTD test subjects than FTC controls or in NDEs of AD test subjects than AC controls.

Figure 1A:
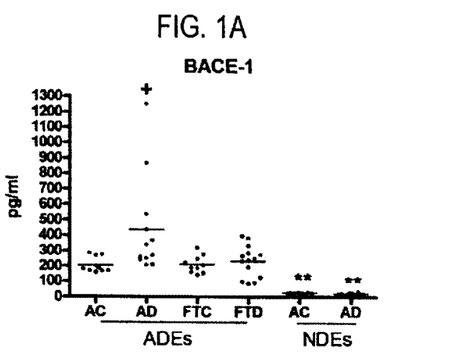
Figure 1B:
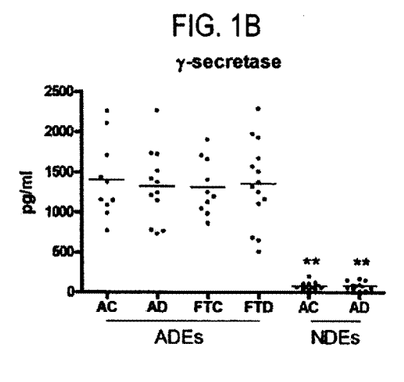
Figures 1C, 1D:
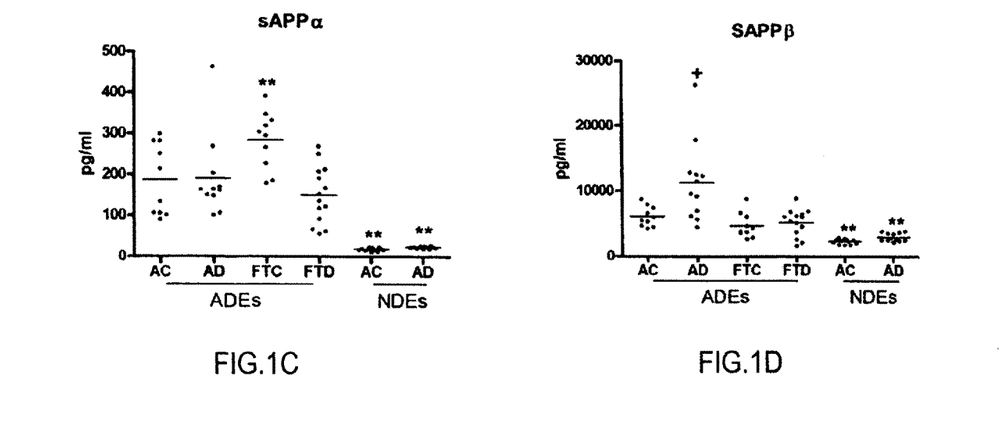
Figure 1E:
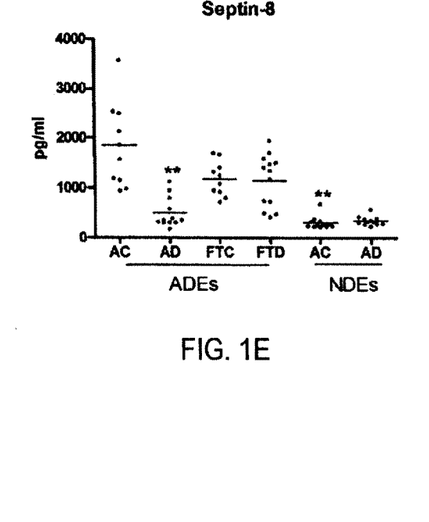
Figure 2A:
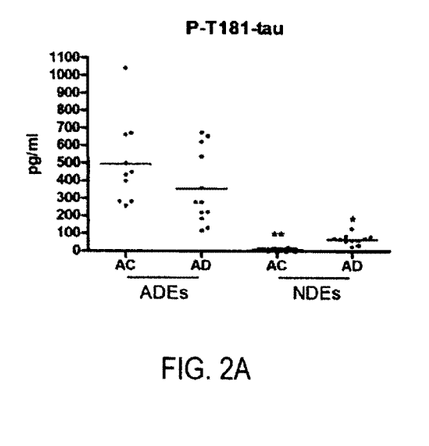
Figure 2B:
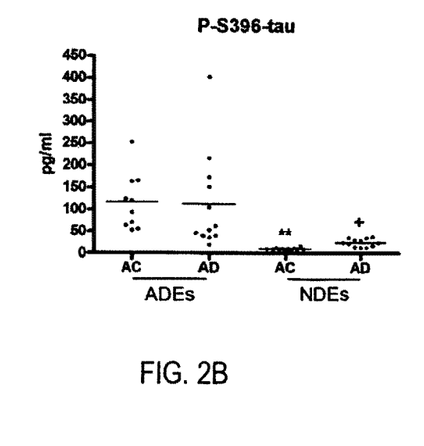
Figure 2C:
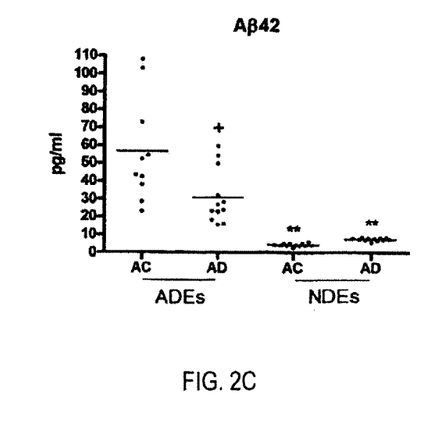
Figure 3:
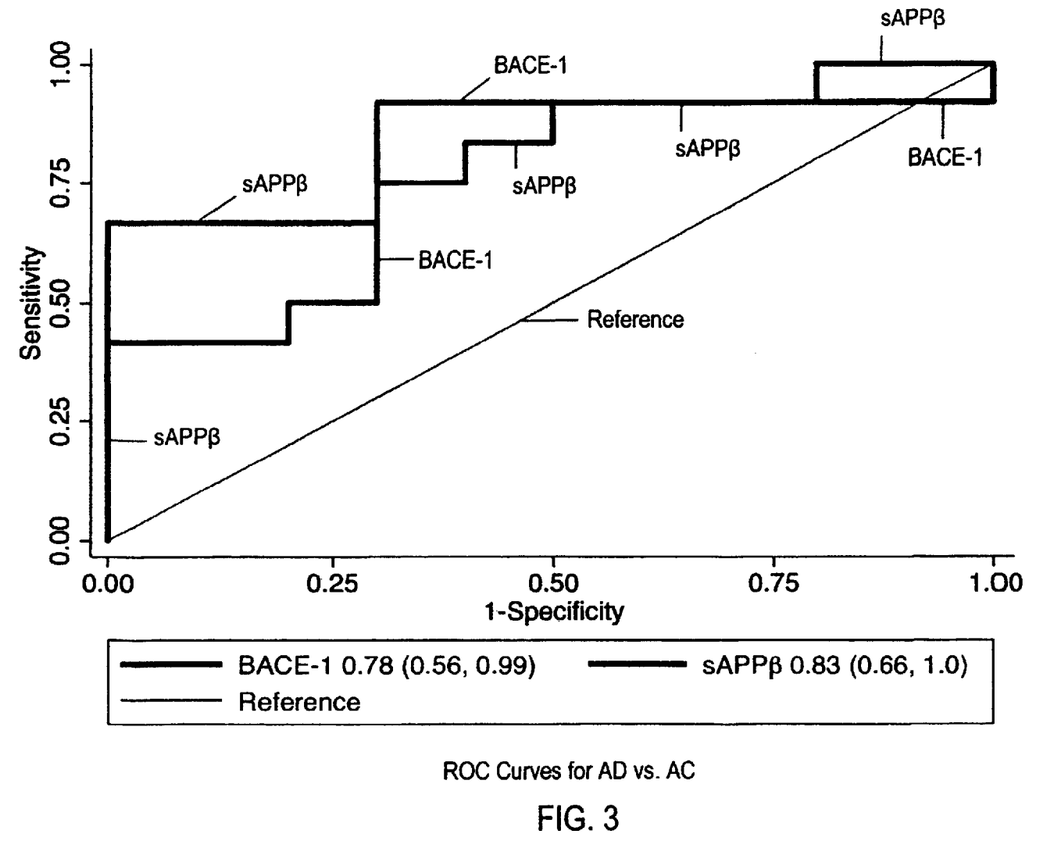
FIGS. 3 and 4 are receiver operating characteristic (ROC) plots showing that both BACE-1 and sAPPβ levels in ADEs significantly distinguish AD test subjects from AC controls, whereas only sAPPβ levels in ADEs distinguish AD test subjects from FTD test subjects.
Figure 4:
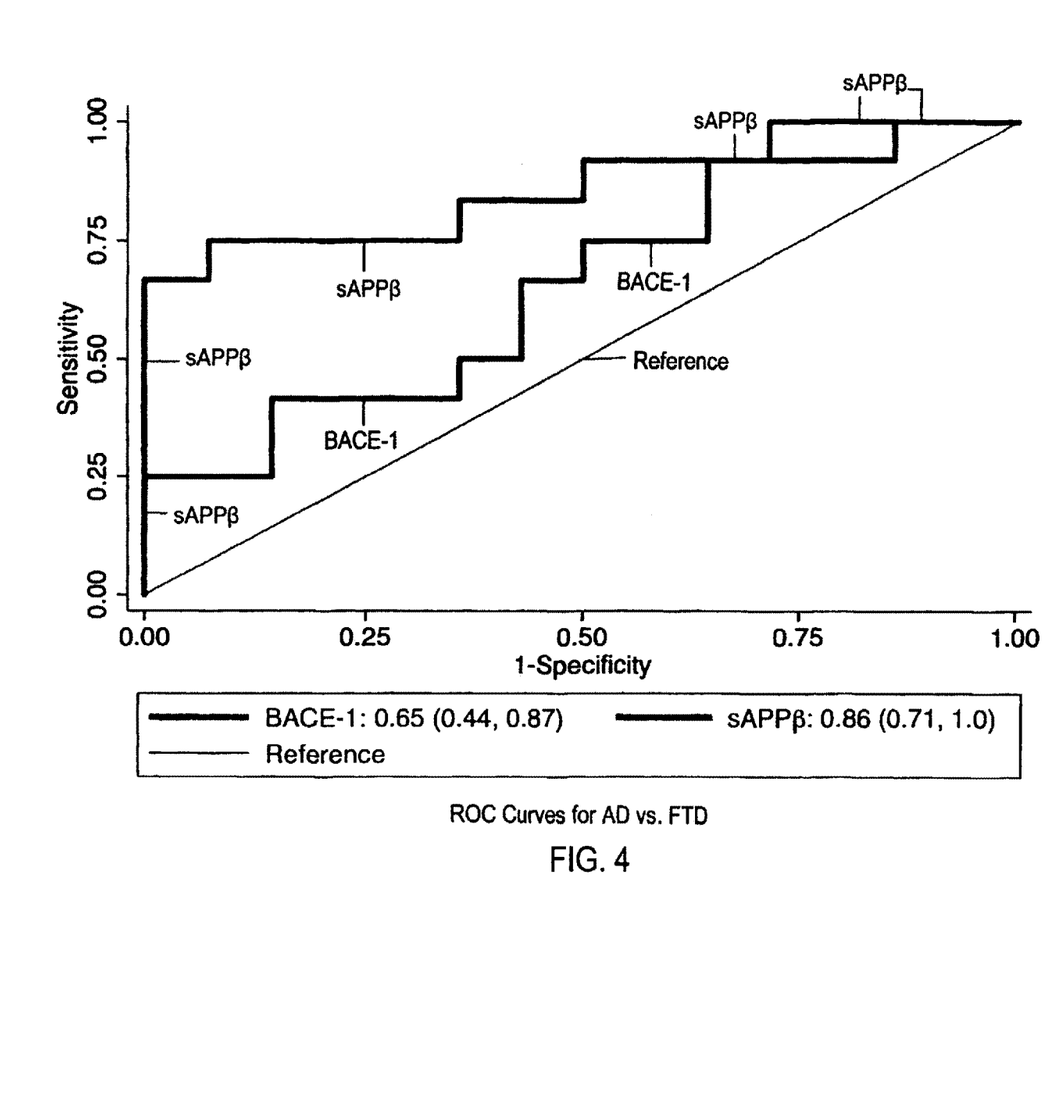

For the three proteins quantified that are putatively pathogenic in AD, levels of each were significantly higher in ADEs than NDEs both in test subjects with AD and in AC control subjects (FIGS. 2A-2C). For each of these proteins, levels in NDEs were significantly higher ($p<0.0001$) in test subjects with AD than in the AC control subjects. In contrast, despite the much higher levels of all three proteins in ADEs than NDEs, only those of Aβ42 distinguished between AD test subjects and AC control subjects where the former had significantly lower concentrations ($p=0.015$) (FIGS. 2A-2C).

As shown in the Experimental Examples above, ADEs have been enriched from the total population of human plasma exosomes in test subjects with AD or FTD and their matched controls by specific positive immunochemical selection (Tables 1 and 2). Plasma ADEs have the same size characteristics and CD81 exosome marker level as NDEs. Purified ADEs prominently express the expected GFAP and GluSyn astrocyte markers, but not neuronal markers found at high levels in NDEs. The most striking finding in ADEs of both test subjects and their controls is up to ten-fold higher concentrations of BACE-1 and γ-secretase components of the pathogenic Aβ42-generating system than in NDEs, and of similarly elevated levels of sAPPβ produced by initial BACE-1 cleavage of APP (FIGS. 1A-1E). Importantly, levels of BACE-1 and sAPPβ are significantly higher in ADEs of AD test subjects than their AC controls (FIGS. 1A-1E). In contrast, levels of the physiological sAPPα cleavage product of APP by α-secretase are significantly higher in ADEs than NDEs, but there is no difference between levels in AD test subjects and AC controls. The putatively pathogenic proteins Aβ42, P-T181-tau and P-S396-tau also are present at much higher levels in ADEs than NDEs of AD test subjects and AC controls, but only levels of Aβ42 differed in AD test subjects and in fact were lower than in AC controls (FIGS. 2A-2C). As was already demonstrated, NDE levels of these same three proteins all are significantly higher in AD test subjects than their AC controls (FIGS. 2A-2C).

The diverse mechanisms expected to mediate elevation of BACE-1 in ADEs of AD test subjects compared to AC controls remain to be elucidated. However, it is of interest that ADE levels of septin-8 were significantly lower in AD test subjects than AC controls (FIGS. 1A-1E). Septin-8 is one member of a family of conserved GTPases implicated in synaptic vesicular trafficking and plasticity. Each of the four transcript variants of septin-8, termed TV1-4, alters levels of BACE-1 in neural cells differently by post-translational mechanisms and coordinately affects levels of sAPPβ and Aβ peptide. A decreased level of total septin-8 protein in ADEs of AD patients correlates best with lower levels of TV1 mRNA documented in autopsy brain tissue from AD test subjects and a consequently higher level of BACE-1. In analyses of the same brain tissues, TV2-4 mRNAs were increased in AD test subjects which also would increase the level of BACE-1 but consequent increases in TV2-4 proteins are not consistent with our findings of a lower level of total septin-8 proteins. The overall network of factors regulating BACE-1 expression is quite complex, however, as SP-1 and NFAT3 transcriptionally enhance levels of BACE-1 and ubiquilin-1 stabilizes BACE-1 protein post-translationally.

The much higher levels of BACE-1, γ-secretase and sAPPβ in ADEs than NDEs suggest that astrocytes are one prominent source of the Aβ42-generating system in neurons through exosomal intercellular transport. The higher ADE levels of BACE-1 and sAPPβ for AD test subjects than AC controls may explain in part the higher levels of the Aβ42-generating system in neurons affected by AD. Neurons are exposed for long periods to much greater amounts of components of the Aβ42-generating system in ADEs than are exported in their NDEs, so that ADEs are likely to be the major vehicle for astrocyte to neuron transport of the Aβ42-generating system. Optimal astrocyte-neuron interactions through ADE trafficking may require astrocyte phenotypic changes to a previously postulated state of activation.

II. Astrocyte Contribution to Neuronal Amyloid Peptide Generation in AD

Further to providing low-risk inexpensive biomarkers that accurately predict risk of AD and facilitate preventative treatments, an assessment of pathogenic proteins in NDEs from plasma has been made. NDE levels of β-amyloid 42 (Aβ42), phosphorylated tau, and other neuropathic proteins reflect neuronal level and efficiency of exosomal loading of each protein. Plasma NDE levels of such proteins are abnormal in AD test subjects relative to those of control subjects up to a decade prior to cognitive losses.

Levels of some proteases involved in the generation of neuropathogenic Aβ42, such as β-site amyloid precursor protein (APP) cleaving enzyme 1 (BACE-1), recently were found to be higher in ADEs than in NDEs despite the lower levels of Aβ42 in astrocytes than neurons in AD test subjects. Astrocyte disposal of components of the Aβ42-generating system through ADEs is considered more efficient than neuronal disposal through NDEs. Further, neurons were determined to avidly take up ADEs, and thus, ADEs transfer proteins from astrocytes to neurons and maintain elevated levels of neuronal Aβ42-generating proteases in AD. The relationship between levels of ADE BACE-1 and NDE Aβ42 in 28 test subjects with cognitive and CSF Aβ42 evidence of early AD and 28 cognitively normal age- and gender-matched controls were studied and the following results obtained: (1) ADE levels of the initial and rate-limiting protease, BACE-1, that generates neurotoxic amyloid peptide, Aβ42, from the large protein precursor, APP, are much higher than BACE-1 levels in NDEs; since ADEs are taken up efficiently by neurons and astrocytes that produce ADEs surround neurons in brain pathways, BACE-1 in ADEs is considered the main source of BACE-1 in neurons; (2) the role of ADE BACE-1 in neuronal generation of neurotoxic amyloid peptide is supported by the strong relationship between levels of ADE BACE-1 and NDE/neuronal Aβ42 (see FIGS. 5 and 6); and (3) ADE BACE-1 is an easily measurable quantity that may predict responses to BACE-1 inhibitor drugs in AD test subjects and also is easily followed as a test of biochemical effectiveness of such drugs.

Experimental Procedure

Levels of Aβ42 in plasma NDEs, normalized for the different quantity of exosome marker CD81 in each preparation, are significantly higher ($p<0.0001$ by t test) in AD test subjects (59.8±6.74 pg/ml, mean±S.E.M.) than in controls (23.7±4.79 pg/ml). There is no significant difference between NDE levels of the Aβ42-generating protease BACE-1 protein in AD test subjects compared to controls. However, elevated Aβ42 production in establishing higher neuronal levels of Aβ42 in AD test subjects is significantly higher NDE levels of sAPPβ, an initial product of BACE-1 cleavage of APP, in AD test subjects (1214±226 pg/ml) than controls (365±45.4 pg/ml) (p=0.0005). Pearson correlation analyses between levels of Aβ42 and of BACE-1 in NDEs also were significant for AD test subjects (r=0.394, p=0.0284) and controls (r=0.513, p=0.0052) in determination of neuronal levels of Aβ42 by production.

ADE BACE-1 levels of 506±67.0 pg/ml (mean±S.E.M.) for AD test subjects are higher than those of 343±43.7 pg/ml for controls (p=0.0422), and both are higher (p<0.0001) than similar BACE-1 levels for NDEs in AD test subjects (42.2±2.88 pg/ml) and controls (52.5±7.10 pg/ml). sAPPβ levels of ADEs also are much higher in AD test subjects (9868±1412 pg/ml) than in controls (1620±238 pg/ml) (p<0.0001). Pearson correlation analyses demonstrated a very strong relationship between ADE BACE-1 levels and NDE Aβ42 levels in AD test subjects (r=0.880, p<0.0001) and in controls (r=0.782, p<0.0001) (FIGS. 5 and 6) which ADEs a prominent source of neuronal BACE-1 in AD test subjects and in controls. No relationship was found between ADE levels of γ-secretase, which liberates Aβ42 after BACE-1 action, and NDE levels of Aβ42.

Without being bound by theory, it is considered that ADEs are taken up by neurons which increases activity of BACE-1 sufficiently to enhance neuronal generation and accumulation of Aβ42. For example, inactivation of ADE BACE-1 prior to neuronal uptake of ADEs in cultured cell systems is expected to reduce resultant increments in neuronal levels of Aβ42. Administration of BACE-1 inhibitors in mouse models of AD is expected to suppress levels of ADE BACE-1 activity and of NDE Aβ42 in parallel. This role of astrocytes plasma ADE levels of BACE-1 in AD test subjects to those with the highest levels for initial preventative therapeutic treatment with BACE-1 inhibitors.

Figure 5:
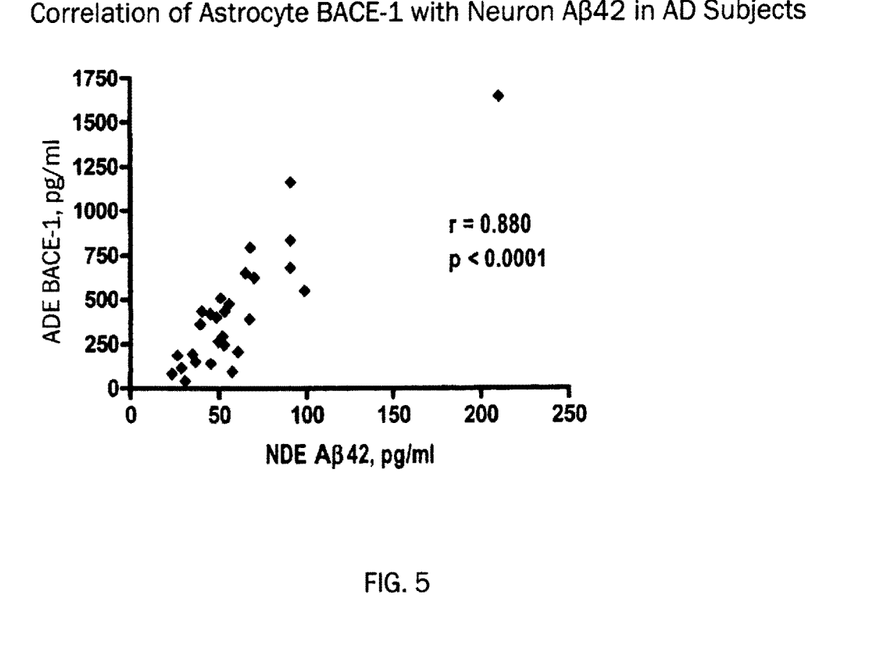
FIG. 5 shows correlation of astrocyte BACE-1 with neuron Aβ42 in AD test subjects.
Figure 6:
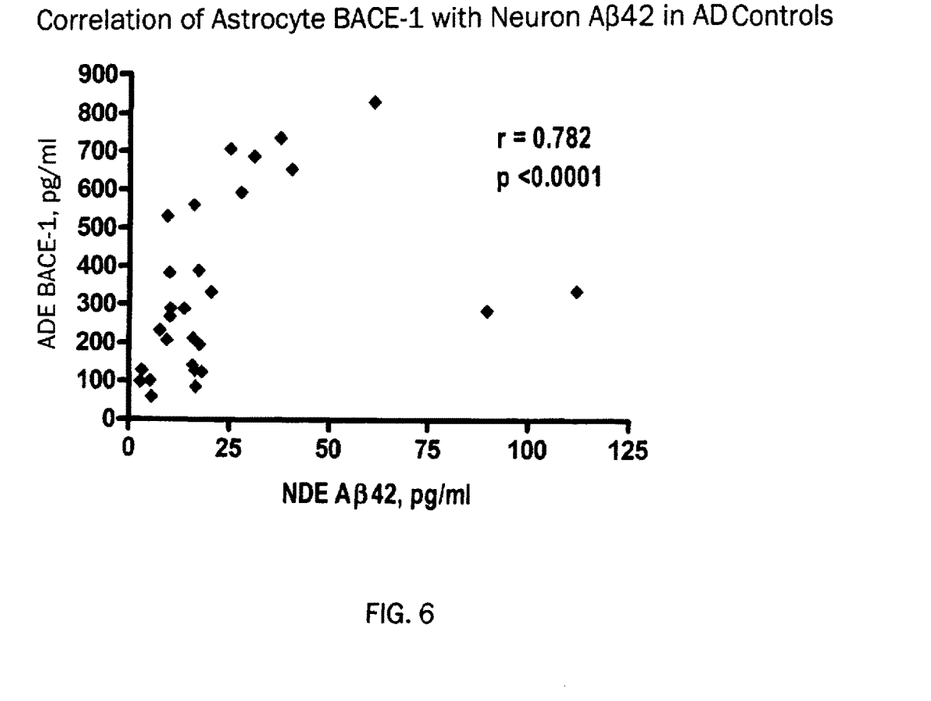
FIG. 6 shows correlation of astrocyte BACE-1 with neuron Aβ42 in AD controls.

In FIGS. 5 and 6, each point depicts the ADE concentration of BACE-1 (Y axis) and the NDE concentration of Aβ42 (X axis) for a single test subject (FIG. 5) or control (FIG. 6). Values of r and p were calculated by a standard formula for the Pearson correlation coefficient after exclusion of the two outlier points in FIG. 6.

Therefore, the present invention has diagnostic and therapeutic value as apparent from the series of interactions among microglia, astrocytes, neurons, and molecular signals which mediate and regulate neurocellular damage in AD and related spectrum of proteinopathic neurodegenerative diseases. High levels of APP and BACE-1 have been delivered to neurons efficiently by ADEs. ADEs have levels of components of the Aβ42-producing pathway that are so much higher than those of NDEs normally that they provide these Aβ42-producing proteins to neurons. In AD, ADEs derived from activated astrocytes contain even higher levels of APP and BACE-1 and are taken up by involved neurons in which they can promote abnormally elevated levels of production of Aβ42.

The capacity to quantify in living humans their plasma neuronal- and astrocyte-derived exosomal levels of BACE-1 allow identification of individuals with preclinical or early AD and high brain levels of BACE-1 who will benefit most from preventative use of BACE-1 will be useful in guiding selection of initial therapy, and adjunctive forms of therapy.

The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claims.

It is claimed:

1. A method for screening candidate drugs for treating Alzheimer's disease in a human subject comprising
    (1) obtaining a plasma or serum or cerebrospinal fluid (CSF) sample from the human subject with Alzheimer's disease;
    (2) in a laboratory setting
    (a) isolating from the plasma or serum or CSF sample central nervous system originated astrocyte-derived exosomes (ADEs), wherein said isolating of said ADEs comprises physical precipitation followed by immunochemical enrichment of said ADEs using antibody against glutamine aspartate transporter (anti-GLAST antibody) based on selective expression of glutamine aspartate transporter (GLAST);
    (b) subjecting protein extracts of said ADEs to enzyme-linked immunosorbent assays (ELISAs) for detection of (i) at least one protein selected from the group consisting of cluster of differentiation 81 (CD81), glial fibrillary acidic protein (GFAP), glutamine synthetase (GluSyn), β-site amyloid precursor protein-cleaving enzyme 1 (BACE-1), γ-secretase, soluble amyloid precursor protein β (sAPPβ), soluble amyloid precursor protein α (sAPPα), amyloid beta-peptide 42 (Aβ42), TAU protein phosphorylated at threonine residue 181 (P-T181-tau), TAU phosphorylated at serine 396 (P-S396-tau), ubiquilin-1, and septin-8, and/or (ii) microRNA9 microRNAs (miRNAs); and quantifying a level for each of said at least one protein and/or said miRNAs detected in said ADEs and identifying the level of each of said at least one protein and/or said miRNAs quantified as a normal level or a non-normal level for said at least one protein and/or said miRNAs;
    (c) comparing the levels of said protein and/or said miRNAs quantified in said ADEs with levels of corresponding proteins and/or miRNAs which are present at a normal level in a control sample from a cognitively healthy human subject to establish a statistically significant difference between the levels of the at least one protein and/or said miRNAs of said ADEs and the levels of the corresponding proteins and/or miRNAs in the control sample;
    (e) combining said ADEs having statistically significant levels of at least one protein and/or said miRNAs of (c) with a drug for treating Alzheimer's disease and incubating such combination for a period of time and, thereafter, subjecting extracts of the ADEs treated with the drug and ADEs of the control sample to ELISAs to quantify the at least one protein previously quantified at the non-normal level and/or RNA assays to quantify said miRNAs previously quantified at the non-normal level and comparing the levels of said proteins and/or said miRNAs in the ADEs to those found in the control sample without the drug to determine effect or lack of effect of said drug on the non-normal levels of said at least one protein and/or said miRNAs.

2. The method of claim 1, wherein the levels in the ADEs of the at least one protein and/or said miRNAs is decreased in a statistically significant amount when compared to the levels of the corresponding proteins and/or miRNAs in the control sample.

3. The method of claim 1, wherein said at least one protein is BACE-1, γ-secretase, sAppβ, sAPPα, or Aβ42.

4. A method for screening candidate drugs for treating Alzheimer's disease in a human subject comprising (1) administering a drug for treating Alzheimer's disease to a human subject with Alzheimer's disease where said drug is being screened to determine if the drug suppresses generation of and/or enhances degradation of astrocyte-derived exosome (ADE) levels of at least one protein and/or at least one microRNA (miRNA) which is present at a non-normal level in said ADE wherein said at least one protein is selected from the group consisting of β-site amyloid precursor protein-cleaving enzyme 1 (BACE-1), γ-secretase, soluble amyloid precursor protein β (sAPPβ), soluble amyloid precursor protein α (sAPPα), amyloid beta-peptide 42 (Aβ42), TAU protein phosphorylated at threonine residue 181 (P-T181-tau), TAU phosphorylated at serine 396 (P-S396-tau), ubiquilin-1, and septin-8;

(2) obtaining a plasma or serum or cerebrospinal fluid (CSF) sample from the human subject with Alzheimer's disease;

(3) in a laboratory setting (a) isolating from the plasma or serum or CSF sample central nervous system originated astrocyte-derived exosomes (ADEs), wherein said isolating of said ADEs comprises physical precipitation followed by immunochemical enrichment of said ADEs using antibody against glutamine aspartate transporter (anti-GLAST antibody) based on selective expression of glutamine aspartate transporter (GLAST);

(b) subjecting protein extracts of said ADEs to enzyme-linked immunosorbent assays (ELISAs) to detect said at least one protein and/or RNA assays for at least one miRNA in said ADEs being screened, and quantifying said at least one protein and/or said at least one miRNA and identifying a level of the protein and/or the miRNA as present in said ADEs at a normal level or a non-normal level;

(c) comparing the level of the protein and/or the level of the miRNA identified in said ADEs following administration of the drug with a level of a corresponding protein and/or miRNA which is taken from the human subject with Alzheimer's disease prior to said administering of the drug to the human subject and with a level of a corresponding protein and/or miRNA which is present in a control sample obtained from a cognitively healthy human subject, to determine if there are or are not statistically significant differences between the levels of the at least one protein and/or said at least one miRNA of said ADEs following administration of the drug, the levels of the corresponding protein and/or miRNA prior to drug treatment of the human subject with Alzheimer's disease and those corresponding which are present in the control samples, thereby indicating effectiveness or non-effectiveness of the drug.

5. The method of claim 4, wherein said at least one protein in said ADE is BACE-1, γ-secretase, sAppβ, sAPPα, or Aβ42.

* * * * *